US006926892B2

United States Patent
Strobel et al.

(10) Patent No.: US 6,926,892 B2
(45) Date of Patent: Aug. 9, 2005

(54) **PROTECTING PLANTS FROM OOMYCETE PATHOGENS BY TREATMENT WITH COMPOSITIONS CONTAINING SERRATAMOLIDE AND OOCYDIN A FROM *SERRATIA MARCESCENS***

(75) Inventors: Gary A. Strobel, Bozeman, MT (US); Steven L. Morrison, San Diego, CA (US); Melanie Cassella, New York, NY (US)

(73) Assignee: HMV Corporation, Alpine, UT (US)

( * ) Notice: Subject to any disclaimer, the term of this patent is extended or adjusted under 35 U.S.C. 154(b) by 5 days.

(21) Appl. No.: 10/144,751

(22) Filed: May 15, 2002

(65) Prior Publication Data

US 2003/0049230 A1 Mar. 13, 2003

Related U.S. Application Data

(63) Continuation-in-part of application No. 09/858,871, filed on May 17, 2001, now Pat. No. 6,660,263.
(60) Provisional application No. 60/291,309, filed on May 17, 2001, and provisional application No. 60/205,102, filed on May 18, 2000.

(51) Int. Cl.[7] .................. A01N 63/00; A01N 43/00; C12P 1/00; C12P 21/04; C12N 1/20
(52) U.S. Cl. .................. 424/93.4; 435/41; 435/71.2; 435/881; 514/9; 514/183; 514/553
(58) Field of Search .................. 424/93.6, 93.4; 435/71.2, 41; 514/881, 9, 183, 553

(56) References Cited

U.S. PATENT DOCUMENTS

| 5,869,038 A | 2/1999 | Leifert et al. |
| 6,060,051 A | 5/2000 | Heins et al. |

OTHER PUBLICATIONS

Stedman's Medical Dictionary, 1982. Williams and Wilkins, Baltimore, p. 1181, Col. 2, Lines 31–32.*
C.H. Hassall, et al. The Conformation of Serratamolide and Related Cyclotetradepsipeptides in Solution, *Phys. Org.*, p. 1757–1761.
Gary Strobel, et al. "Oocydin A, a chlorinated macrocyclic lactone with potent anti–oomycete activity from *Serratia marcescens*", Microbiology (1999), 145, pp. 3557–3564.

* cited by examiner

*Primary Examiner*—David Naff
*Assistant Examiner*—Kailash C. Srivastava
(74) *Attorney, Agent, or Firm*—McDermott Will & Emery LLP (57) ABSTRACT

A method is provided to protect plants from oomycete pathogens by treating plants with a composition comprising serratamolide. The composition may also contain oocydin A obtained from *Serratia marcescens* MSU-97.

12 Claims, 9 Drawing Sheets

Serratamolide
Cyclic (D-β-hydroxydecanoyl-L-seryl-D-β-hydroxydecanoyl-L-seryl)

FIG. 1

Oocydin

PROTECTING PLANTS FROM OOMYCETE PATHOGENS BY TREATMENT WITH COMPOSITIONS CONTAINING SERRATAMOLIDE AND OOCYDIN A FROM *SERRATIA MARCESCENS*

This application claims priority to U.S. provisional patent application Ser. No. 60/291,309, filed May 17, 2001, and is a Continuation-In-Part and claims priority to U.S. application Ser. No. 09/858,871, filed May 17, 2001, now U.S. Pat. No. 6,660,263, which claims priority to U.S. Provisional Application Ser. No. 60/205,102, filed May 18, 2000.

FIELD OF THE INVENTION

This invention relates generally to the protection of plants from pathogen attack, and particularly to protection from Oomycete pathogens, including treating plants with compositions from *Serratia marcescens*. Thus, the invention is concerned with a new group of antifungal and antimycotic compositions.

BACKGROUND OF THE INVENTION

One of the largest problems facing agriculture today is effective control of plant pathogens. Compounds that are biologically derived and toxic only to specific target organisms are preferred for control of plant pathogens, because of their decreased impact on the environment and on non-target organisms.

Plants, especially those growing in freshwater environments, must have disease resistance mechanisms to cope with aquatic plant pathogenic organisms that may invade and destroy them. Oomycetes would be expected to attack plants that normally exist in strictly aquatic environments. However, aquatic plants seem to thrive and be relatively disease free in these ecosystems. This biological conundrum may be related to extrinsic factors controlling plant disease resistance. Epiphytic or endophytic microbes may associate with aquatic plants and produce antioomycetous compounds. If such compounds exist, they may prove agriculturally applicable to plant disease control situations in which Oomycetes are a problem.

Metalaxyl is well established as the agent to which the Oomycetes are the most sensitive. However, increasing resistance to metalaxyl is developing in certain Oomycete populations and this agent is being rendered increasingly less effective. Lyr, H., *Modern Selective Fungicides* (Gustav Fischer Verlag: New York, Jena., 1995). Thus, a need exists for new compounds to combat these plant pathogens.

SUMMARY OF THE INVENTION

The present invention provides *Serratia marcescens* and its isolates as being useful to control and prevent Oomycete infestation of plants, especially including the use of *Serratia marcescens* MSU-97 and serratamolide.

The present invention further describes the production and isolation of serratamolide from *Serratia marcescens* MSU-97, as well as the range and efficacy of its antioomycetous activity. Serratamolide is a cyclic peptide known to have slight antibiotic properties, to inhibit phagocytosis by polymorphonuclear leukocytes and to increase potassium movement out of bacterial membranes. It has been discovered that serratamolide also has previously unknown antioomycetous activity against specific plant pathogens.

Accordingly, the invention provides compounds for use in protection of plants from Oomycete pathogens. The invention also provides a method for making the compounds of the invention and an environmentally desirable method of controlling and preventing Oomycete infestation of plants by using the compounds of the invention.

The invention further provides an environmentally desirable method of controlling and preventing Oomycete infestation of plants by administering the compounds of the invention to plants.

In accordance with the foregoing objects and advantages, the present invention provides a method for the protection of plants from Oomycete pathogens which comprises treating the plants with an effective amount of one or more isolates of *Serratia marcescens*. In further aspects, the present invention also provides an isolated serratamolide from *Serratia marcescens* compositions and use of the serratamolide for the protection of plants from Oomycete pathogens.

DETAILED DESCRIPTION OF THE INVENTION

The present invention describes methods for the protection of plants from Oomycete pathogens by treatment of the plant with a pathogen effective amount of one or more isolates from *Serratia marcescens* which possesses antioomycetous activity against Oomycete plant pathogens. The isolate is any material from *Serratia marcescens* which exhibits antioomycetous activity against Oomycete plant pathogens but is more particularly *Serratia marcescens* MSU-97 or serratamolide, used alone, together, or in admixture or with oocydin A. By effective amount is meant an amount sufficient to protect the plants from Oomycete pathogens.

*Serratia marcescens*. *Serratia marcescens* is a Gram-negative bacillus that occurs naturally in soil and water, as well as in the human intestines. Methods of identifying and classifying *S. marcescens* are known in the art. Falkiner FR (1997) *J. Med. Microbiol.* 46:903-12. Growth of Serratia marcescens is accompanied by the production of a characteristic red tripyrrole pigment called prodigiosin. The production of a number of secondary metabolites is correlated with pigment synthesis. Prodigiosin is synthesized from amino acids, although the complete biosynthetic pathway is unknown. Bermingham, M. A., et al. (1971). *J. Gen. Microbiol.* 67, 319–324.

*Serratia marcescens* isolate 97 (MSU-97) is an epiphytic bacterium isolated from *Rhyncholacis pedicillata*, an aquatic plant native to Venezuela. See, EXAMPLE 1. A biologically pure culture of *Serratia marcescens* MSU-97 is deposited in the culture collection at Montana State University (MSU) and in other national collections. A deposit containing *Serratia marcescens* MSU-97, has been deposited with the Central Bureau of Schimmelcultures (CBS) in the Netherlands and assigned CBS No. 112860. The subject cultures are deposited under conditions that ensure that access to the cultures will be available during the pendency of the patent application disclosing them to one determined by the Director of the USPTO to be entitled thereto under 37 C.F.R. §1.14 and 35 U.S.C. §122. The deposits are available as required by foreign patent laws in countries where counterparts of the subject application, or its progeny, are filed. However, the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least 30 years after the date of deposit or for the enforceable life of any patent which may issue disclosing the cultures plus 5 years after the last request for a sample from the deposit. The depositor acknowledges the duty to replace the deposits should the depository be unable to furnish a sample when requested, due to the conditions of the deposits. All restrictions on availability to the public of the subject culture deposits will be irrevocably removed upon granting of a patent disclosing them.

Figure 1:
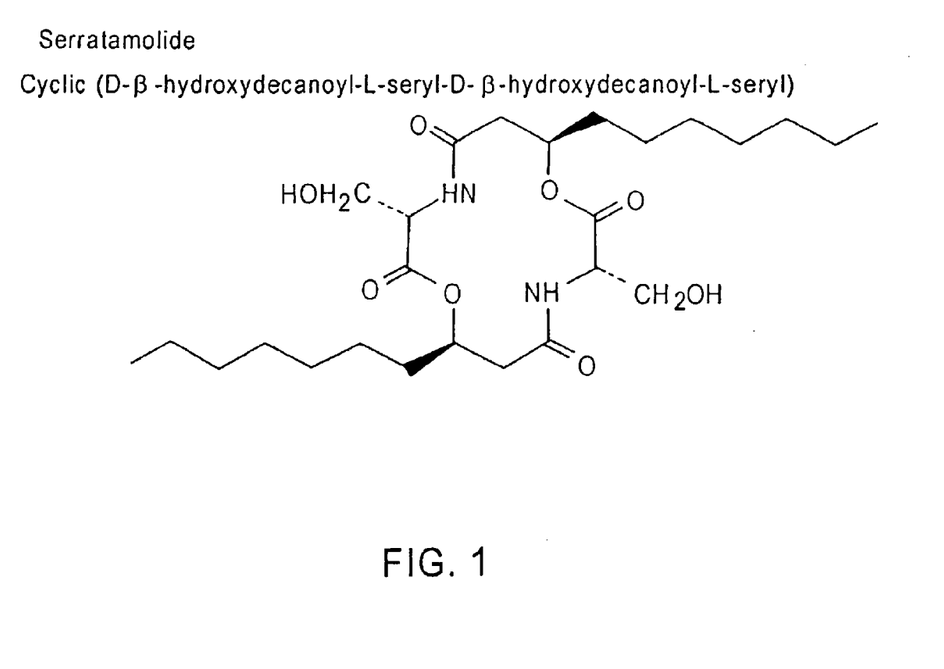
FIG. 1 shows the structure of serratamolide.

In one aspect, the compositions of the invention contain serratamolide (FIG. 1), which has antioomycetous activity, as shown in EXAMPLE 2. In one embodiment, the concentration of serratamolide is between 6 and 100 $\mu$g/ml.

Figure 2:
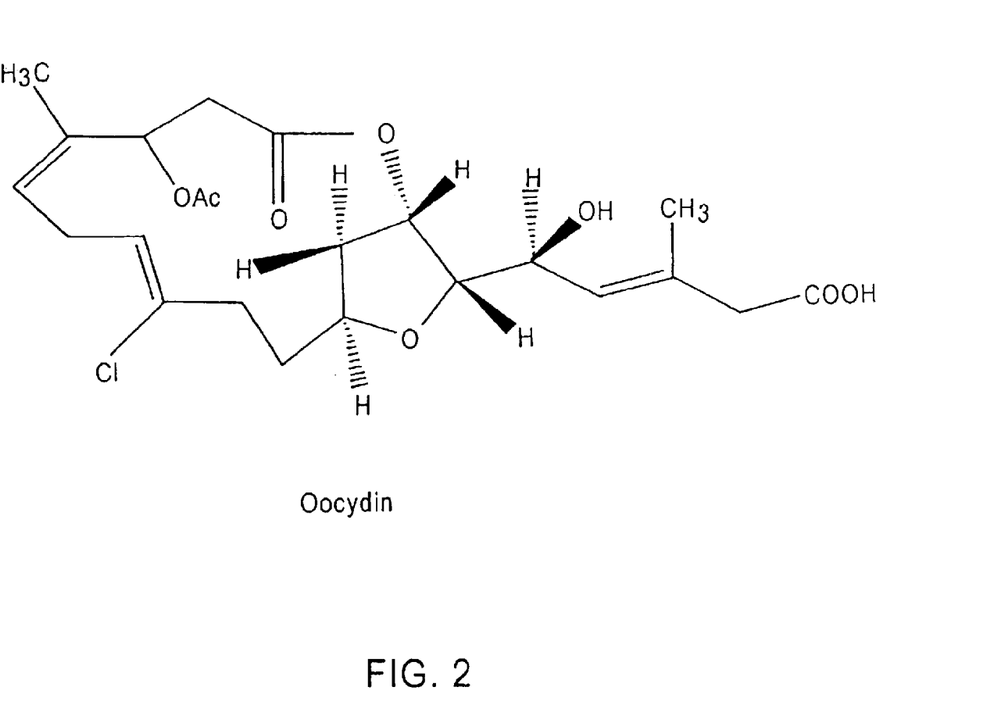
FIG. 2 shows the structure of oocydin A (no absolute stereochemistry is implied).

The compositions of the invention may also contain a mono-chlorinated lipophilic macrocyclic lactone, oocydin A (FIG. 2), which was isolated from *Serratia marcescens*. See, Strobel, G. et al. (1999) *Microbiol.* 145: 3557–3564. In culture, *Serratia marcescens* MSU-97 produces oocydin A that can be recovered from the culture medium. Overall, it appears that oocydin A has selective lethal activity against Oomycetes at MICs lower or similar to those noted for metalaxyl. Oocydin is fully described in U.S. application Ser. No. 09/858,871, filed May 17, 2001, the disclosure of which is incorporated herein by reference.

The compositions or isolates of the invention may also contain prodigiosin, a red pigment produced by *Serratia marcescens*.

The compounds of the invention may be in a form containing culture medium from which *Serratia marcescens* MSU-97 has been cultured (see, EXAMPLE 1). Alternatively, the compound of the invention may further contain an agriculturally acceptable carrier. Thus, the compound of the invention may be in a form especially prepared for administration to plants, such as the formulations containing solvents, solid carriers and, if appropriate, surface-active compounds (surfactants) (see, below).

*Oomycetes.* The Stramenophila have recently been classified as being a new kingdom of plants. Among the Stramenophila are the Labyrinthulomycota, which have a thallus that is a network of branched tubes within which amoeboid cells crawl. Also among the Stramenophila are the Hyphochytriomycota, which have a thallus that is single-celled or rhizoidal and have motile cells with a single anterior tinsel type flagellum. The Oomycetes are the largest group of Stramenophila. Oomycetes have a thallus that is filamentous with coenocytic hyphae or rarely single-celled or holocarpic. Oomycetes have motile cells, often with whiplash and tinsel flagellae.

There are more than 500 species in the Oomycetes. The Oomycetes include such genera as *Leptomitus, Brevilegnia, Aphanomyces, Achlya, Saprolegnia, Pythium, Plasmopara, Phytophthora,* and *Peronospora*.

The Oomycetes that have undergone extensive life cycle studies have been found to be diploid in the vegetative phase with meiosis occurring during gametogenesis. "Oomycota" means "egg fungi", a term that refers to the large round oogonia, or structures containing the female gametes. Oomycetes are oogamous, producing large non-motile gametes called eggs, and smaller gametes called sperm.

The Oomycota were once classified as fungi, because of their filamentous growth, and because they feed on decaying matter like fungi. The cell wall of Oomycetes, however, is not composed of chitin, as in the fungi, but is made up of a mix of cellulosic compounds and glycan. The nuclei within the filaments are diploid, not haploid as in the fungi.

Oomycetes are found all over the world in fresh-water and salt-water habitats. Oomycetes absorb their food from the surrounding water or soil, or may invade the body of another organism to feed. The presence of free water or high humidity is important for the development and the pathogenicity of these organisms. Some of the terrestrial Oomycetes are among the most important plant pathogens.

Many Oomycetes are important parasites on flowering plants. These include root rotting fungi, seedling dampening mold, blister rusts, white rusts (Albugo, such as *A. candida*), water molds and the downy mildews (including *Peronospora tabacina*) that attack mainly potatoes, tomatoes, vines, hops, maize, sugar beet, tobacco, vegetables, lettuce, but also bananas, rubber, as well as lawns and ornamentals.

Plant diseases caused by Oomycetes can have a major impact on human populations. *Plasmopara viticola* causes the downy mildew of grapes that, in the late 1870s, almost wiped out the French wine industry. *Phytophthora infestans* causes the late blight of potato that, in the summer of 1846, caused the great Irish Potato Famine.

Other species of *Phytophthora* destroy eucalyptus, avocado, pineapples, and other tropical crop plants. *Phytophthera parasitica* causes black shank disease. Root rot of ornamental plants, such as poinsettia, can be caused by *Pythium aphanidermatum, P. debaryanum, P. irregular, P. megalacanthum, P. oligandum, P. perniciorum, P. polymastum* and *P. utimum,* and by *Phytophthora parasitica.* Quick oak decline and ornamental plants are subject to attack by *phytophthora ramorum.*

Accordingly, the compounds of the invention and the methods of using the compounds are useful for protecting or treating Oomycete-related diseases affecting cereals (maize, wheat, barley, rye, oats, rice, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumber, melons); fiber plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as tobacco, nuts, coffee, sugar cane, tea, vines, hops, bananas and natural rubber plants, as well as ornamentals (flowers, shrubs, broad-leaved trees and evergreens, such as conifers). This listing of plants is illustrative but does not represent any limitation on the invention.

Administration of the Compounds of the Invention. The invention offers a number of advantages and uses stemming from the easily controlled administration of the compounds of the invention on in plants or plant tissue, such as in the manner of U.S. Pat. Nos. 5,856,154, 6,031,153, and 6,228,884. Administration may be accomplished simply by applying the compound of the invention to the plant tissue, or to the plant or part of the plant in such a manner and in such an amount as to be effective. For example, application of the compound of the invention can be made to the entire plant (i.e., stem and both sides of the leaves). If administration to the roots is desired, application to the seeds or the soil around the seeds or roots is also possible.

The compounds of the invention can be applied in pure form, in solution or suspension, as powders or dusts, or in other conventional formulations used agriculturally or in bioreactor processes. See, U.S. Pat. No. 5,856,154. The compounds of the invention can be prepared in formulations in a known manner, for example by intimately mixing and/or grinding the active ingredients with extenders, such as, for example, with solvents, solid carriers and, if appropriate, surface-active compounds (surfactants). See, U.S. Pat. No. 6,228,884. Suitable carriers and additives can be solid or liquid and correspond to the substances expediently used in formulation technology, such as, for example, natural or regenerated mineral substances, solvents, dispersants, wetting agents, tackifiers, thickeners, binders or fertilizers. See also, U.S. Pat. No. 6,228,884. Such formulations may include solid or liquid carriers, that is, materials with which the regulator is combined to facilitate application to the plant, tissue, cell or tissue culture, or the like, or to improve storage, handling or transport properties. Examples of suitable carriers include silicates, clays, carbon, sulfur, resins, alcohols, ketones, aromatic hydrocarbons, and the like. If formulated as a conventional wettable powder or aqueous emulsion, the regulator formulation may include one or more conventional surfactants, either ionic or non-ionic, such as wetting, emulsifying or dispersing agents.

As a liquid formulation the compounds of the invention may be applied as a spray to plant leaves, stems or branches, to seeds before planting or to the soil or other growing medium supporting the plant. Alternatively, the administration of the compounds of the invention can be guided by the administration of acylalanine fungicides, such as metalaxyl (N-(2,6-dimethylphenyl)-N-(methoxyacetyl)-DL-alanine methyl ester); benalaxyl (N-(2,6-dimethylphenyl)-N-(phenylacetyl)-DL-alanine methyl ester); furalaxyl (N-(2,6-dimethylphenyl)-N-(2-furanylcarbonyl)-DL-alanine methyl ester). The preferred application of the acylalanine fingicides is foliar application, in which the foliage and the growing plant being treated with the active ingredient. See, U.S. Pat. No. 6,228,884. In the case of soil application, the active ingredient is incorporated into the soil directly by applying it in liquid form, or, for example, by means of granules.

A preferred method of applying the compounds of the invention is to the aerial parts of the plant, especially the foliage (foliar application). See, U.S. Pat. No. 6,228,884. Number and rate of application depend on the biological and climatic environmental conditions for the pathogen. Alternatively, the compounds of the invention may reach the plant via the soil through the root system, by drenching the site of the plant with a liquid composition, or by incorporating the substances into the soil in solid form, for example in the form of granules (soil application).

The compounds of the invention are employed as pure active ingredient or, preferably, together with the adjuvants conventionally used in the art of formulation and is therefore processed in a known manner to give, for example, emulsion concentrates, spreadable pastes, directly sprayable or dilutable solutions, dilute emulsions, wettable powders, soluble powders, dusts, granules, or by encapsulation, for example in polymeric substances. The methods of application, such as spraying, atomizing, dusting, scattering, brushing on or pouring, as well as the type of the compositions, are selected to suit the intended aims and the prevailing circumstances.

As a rule, the agrochemical compositions comprise 0.1 to 99%, in particular 0.1 to 95%, of the active ingredient 99.9 to 1%, in particular 99.9 to 5%, of a solid or liquid additive, and 0 to 25%, in particular 0.1 to 25%. See, U.S. Pat. No. 6,228,884. While concentrated compositions are more preferred as commercially available goods, the end consumer uses, as a rule, dilute compositions.

It is a standard demand in crop protection to achieve an optimal effect with an active ingredient at the lowest dosage rate required while simultaneously keeping the pollution of the environment as low as possible. For in vitro application, the compound of the invention are added quite easily, for example, by applying the compound of the invention to the medium contacting the plant cells. In bioreactor systems, administration can be achieved by a single addition of regulator formulation to the reaction medium or by gradual addition over a predetermined period of time.

One advantage arises from the ability to apply the compounds of the invention during different times of plant development. For example, the synchronization of the application of the compound of the invention with plant development (germination, tillering, sprouting, flower formation, anthesis, fruit ripening, dry down, abscission etc.) can be accomplished.

The compounds of the invention can also be applied to plants in combination with another agent that may afford some benefit to the plant. For example, the compounds of the invention can be admixed with a fertilizer and then applied.

The details of one or more embodiments of the invention are set forth in the accompanying description above. Although any methods and materials similar or equivalent to those described herein can be used in the practice or testing of the invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented in order to more fully illustrate the preferred embodiments of the invention. These examples should in no way be construed as limiting the scope of the invention, as defined by the appended claims.

EXAMPLE 1

*Serratia marcescens* MSU-97

Isolation of *Serratia marcescens* MSU-97. *Rhyncholacis pedicillata* is a small highly specialized aquatic plant of the family Podostemaceae that grows in colonies and thrives in some of the brown-black rivers of the Venezuelan-Guyana. *R. pedicillata* is 0.2–1.0 m in size and it has a bulbous base that anchors the plant to a rock. Its stems are multibranched, are lacy-like, and covered with numerous small leaves.

Close examination of individual plants in the Carrao River revealed animal or environmentally inflicted wounds on the stems. Normally, such wounds would serve as entry points for one or more pathogenic Oomycetes. However, little or no disease symptoms on the plants were observed.

Several small stem fragments of *R. pedicillata* were removed from the plant growing in its river environment and cut into pieces about 5.0 mm. These tissue pieces were then soaked overnight in 0.1 M sodium phosphate buffer (pH 6.8) made 0.1 M with respect to NaCl. After 12 hr, the saline solution was collected, left at 23° C. for 1 hr and then streaked onto a semi-selective medium (King's B (KB)) according to the procedures of Miller, C. M. et al. (1998). *J. Appl. Microbiol.* 84, 937–944.

After 2 days, the most commonly appearing colonies consisted of bacilliform bacteria that were producing a bright red pigment. The red-pigment producing bacterial strain was identified as *Serratia marcescens*. Standard isolates of *S. marcescens*, used for comparative purposes, were obtained from the MSU bacterial culture collection, Dept of Microbiology, Montana State University, Bozeman, Mont.

Each of these colonies was transferred back to the KB medium and incubated for several days prior to being transferred as individual colonies onto potato dextrose agar plates (PDA). These PDA plates were incubated for at least 3–5 days at 23° C. prior to having the PDA plate co-inoculated (as 5.0×5.0 infested agar plugs) with a rapidly growing culture of *Pythium ultimum*. The co-inoculated culture plates were then incubated at 23° C. and examined for antioomycetous activity. Bacterial colonies producing zones of inhibition around them were considered positive for antioomycetous activity.

Several antioomycetous activity-producing bacteria were isolated from *R. pedicillata*, but *S. marcescens* was by far the most prevalent. One isolate *S. marcescens*, (MSU-97), produced impressive zones of inhibition when challenged with *P. ultimum* in plate bioassay tests. Inhibition zones were retained on the plates at 23° C. until the agar in the plate desiccated (after 4–6 weeks). *P. ultimum* did not develop any further on the plates when challenged with isolate 97 than that of its original zone of inhibition appearing after 2–3 days.

The isolate of *S. marcescens* is stored in the MSU bacterial culture collection as acquisition no. 97.

Since *S. marcescens* is a relatively common microorganism. Regular isolates of it were also screened in the antioomycetous plate test. Neither ATCC isolate 1009, nor MSU isolate 69 demonstrated any antioomycetous activity diffusing from the culture after 3 days of exposure to *P. ultimum*. This straightforward antifungal test revealed that the likelihood of finding one or more novel antioomycetous substances from isolate 97 of *S. marcescens* was extremely unlikely.

Scanning electron microscopy. Materials to be examined were placed in 2% glutaraldehye in 0.1 M sodium cacodylate buffer (pH 7.2–7.4) (Upadhyay, R. V. et al. (1993). *Mycol. Res.* 95, 785–791). The samples were critical point dried, gold coated with a sputter coater and observed and photographed with a JEOL 6100 scanning electron microscope. Bacterial preparations were supported on dried γ-irradiated carnation leaves that served as a support for the cells.

SEM examination of the surface of some small stems of *R. pedicillata* revealed that bacterial colonies were in abundance. Hundreds of individual cells seemed to constitute each colony. Individual bacterial cells also appeared on the plant surface. *Serratia marcescens* colonized the surface of the stems of *R. pedicillata*, in contrast to being internal to them.

The surface characteristics of the bacteria on the plant were identical to those on bacterial surfaces of pure cultures of authentic *S. marcescens* (isolate 97). The bacterial surface characteristics included multiple small projections as well as a generally relatively rough cell surface. This does not appear to be common in bacteria and this characteristic may serve as a means to help locate and identify *S. marcescens* on the surface of its host. In addition, the size and shape of the bacterial cells on the plant and those of the authenticated culture appear to be identical. Since *S. marcescens* was primarily recovered from the plant surface and not from internal tissues, it was considered more epiphytic than endophytic in its relationship to the plant.

EXAMPLE 2

Serratamolide Isolated from Liquid Cultures of *Serratia marcescens*

The production and localization of serratamolide in *Serratia marcescens* MSU-97 as well as the range and efficacy of its antioomycetous activity were examined. Serratamolide was found to have previously unknown antioomycetous activity against specific plant pathogens.

Figure 3:
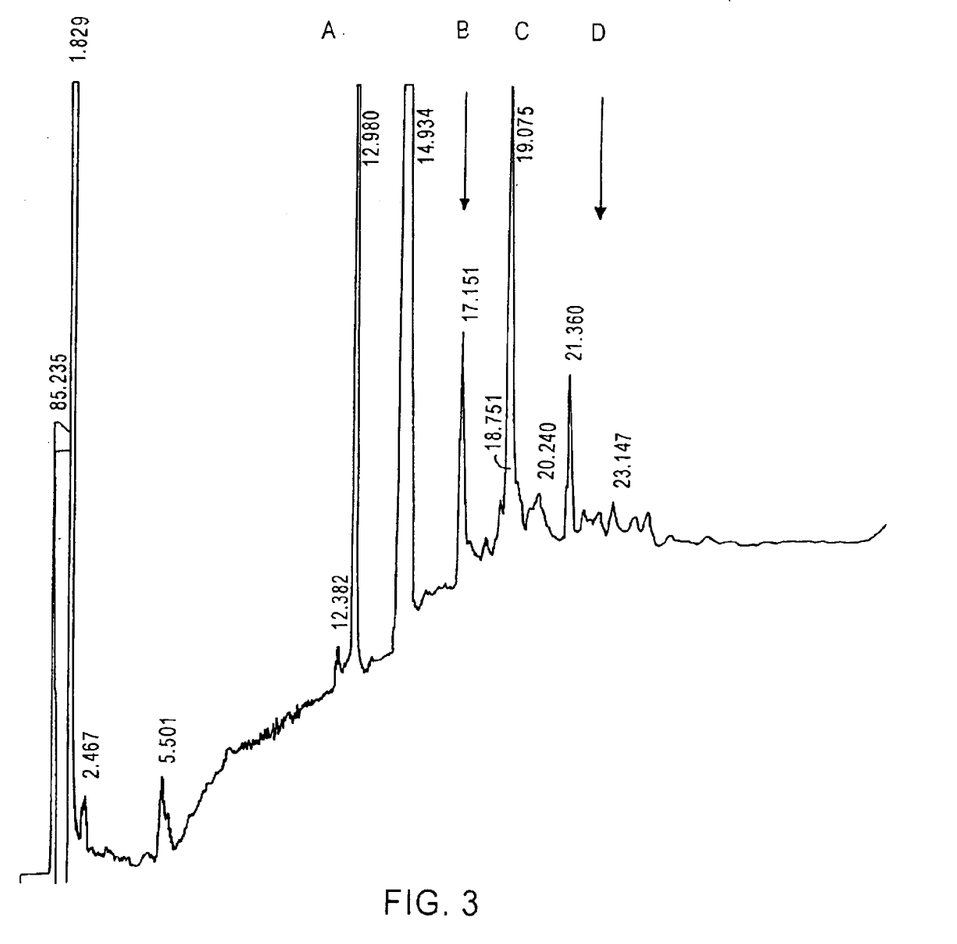
FIG. 3 is a chromatogram of antioomycetous compounds produced by *S. marcescens* MSU-97 isolated and characterized against *P. ultimum*. Growth of *S. marcescens* was in soytone medium. (A) oocydin; (B) unknown component; (C) serratamolide; (D) unknown component. The presence of oocydin was confirmed by co-chromatography against an authentic standard. The presence of serratamolide was confirmed as described in EXAMPLE 2.
Figure 4:
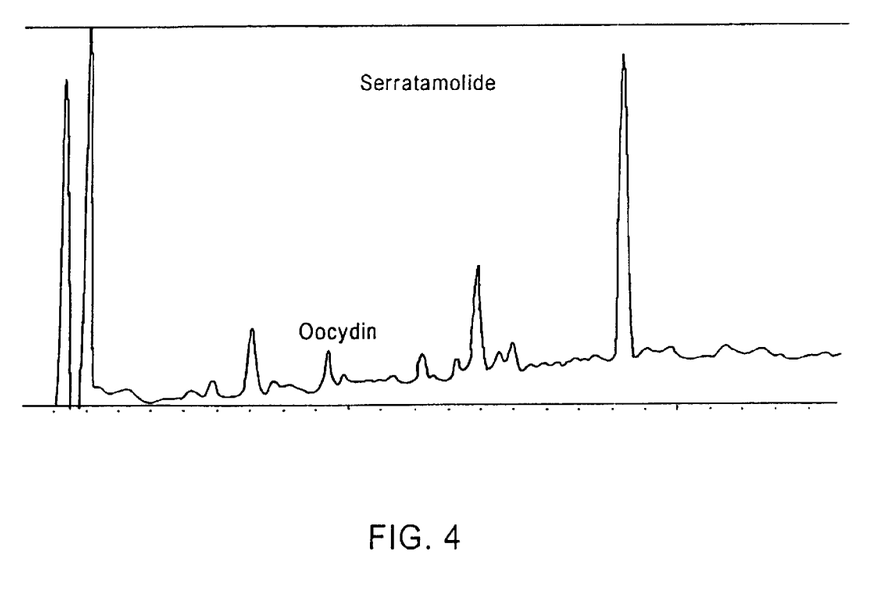
FIG. 4 is a chromatogram showing separation of serratamolide by preparative HPLC.
Figure 5:
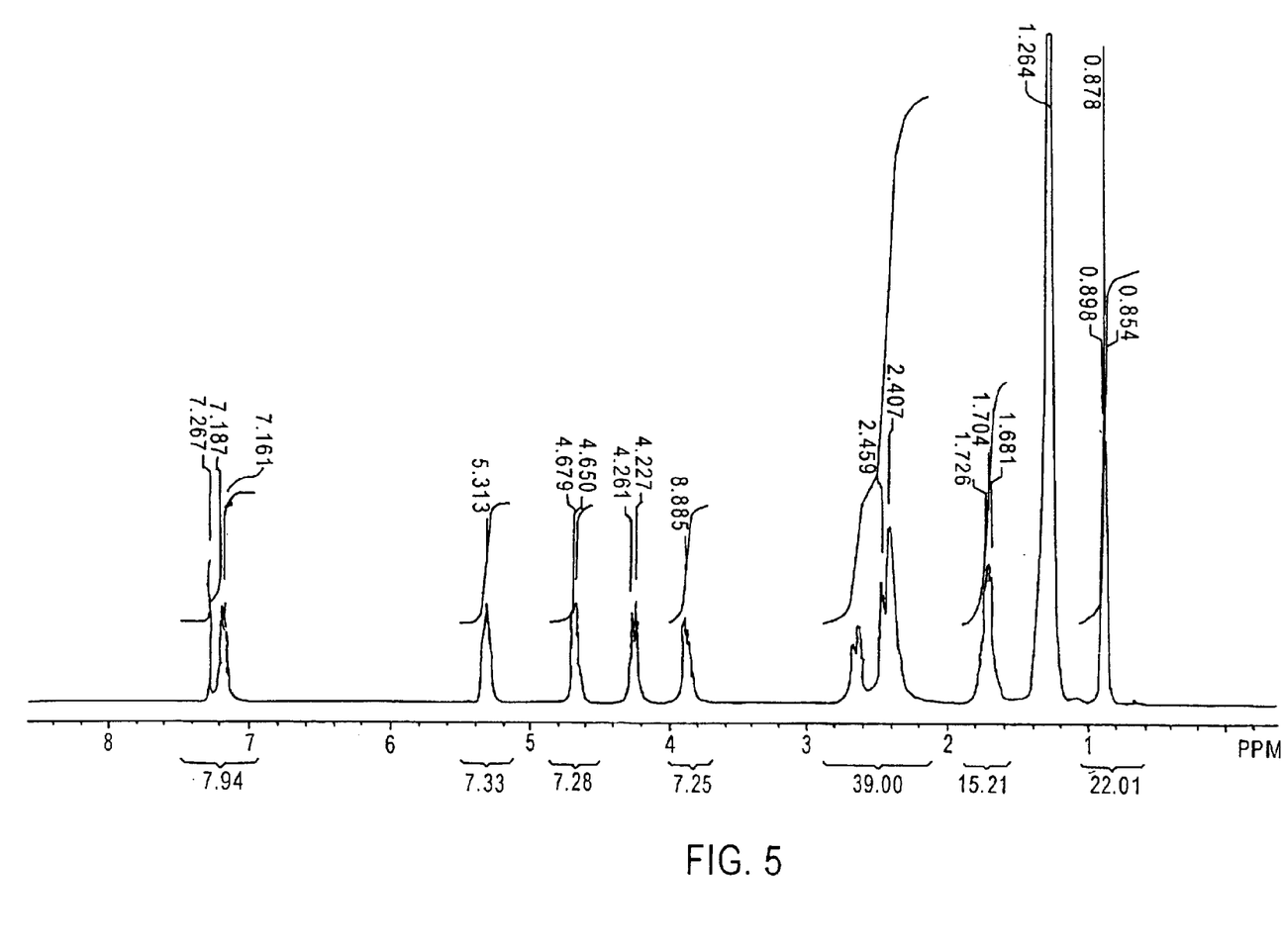
FIG. 5 is a $^1$H-NMR spectrum of serratamolide obtained in 100% deuterated chloroform.
Figure 6:
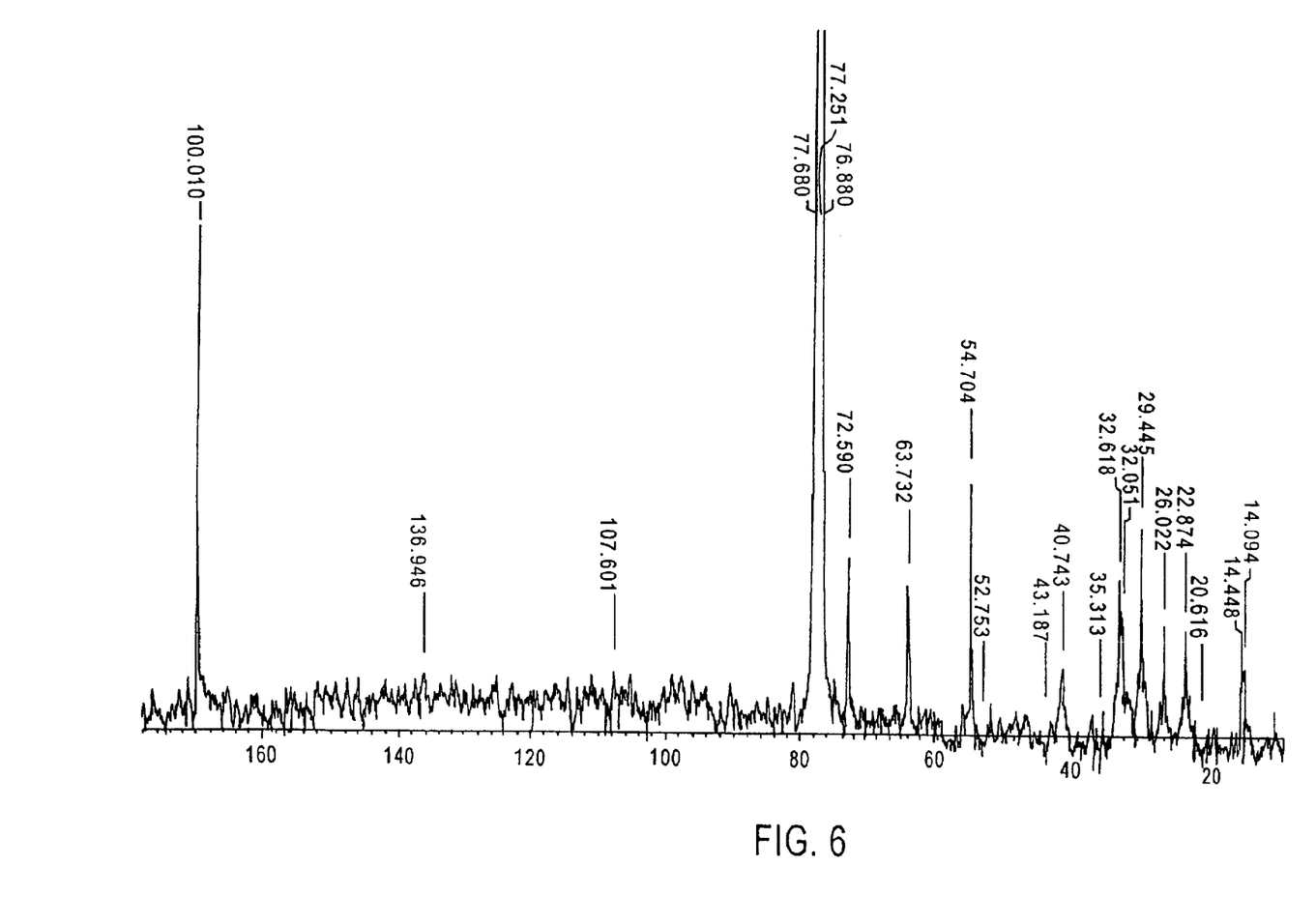
FIG. 6 is a $^{13}$C-NMR of serratamolide isolated from *S. marcescens* MSU-97. Serratamolide was dissolved in 100% deuterated chloroform. A serratamolide fraction hydrolyzed for 30 minutes in 0.3 N NaOH and rechromatographed by analytical HPLC showed the absence of a serratamolide peak. In addition, acid hydrolysis in 10 N HCl of the purified fraction released serine. Serine was identified by paper chromatography on Whatman 3MM paper in n-butanol, acetic acid, water (4:1:2 v/v). In this solvent system, serine ran with a $R_F$ of 0.92, and was identified by its reaction with 0.1% ninhydrin dissolved in absolute ethanol. Both the base and acid hydrolyzed fractions lost the ability to inhibit growth of *P. ultimum* in clearing assays.
Figure 7:
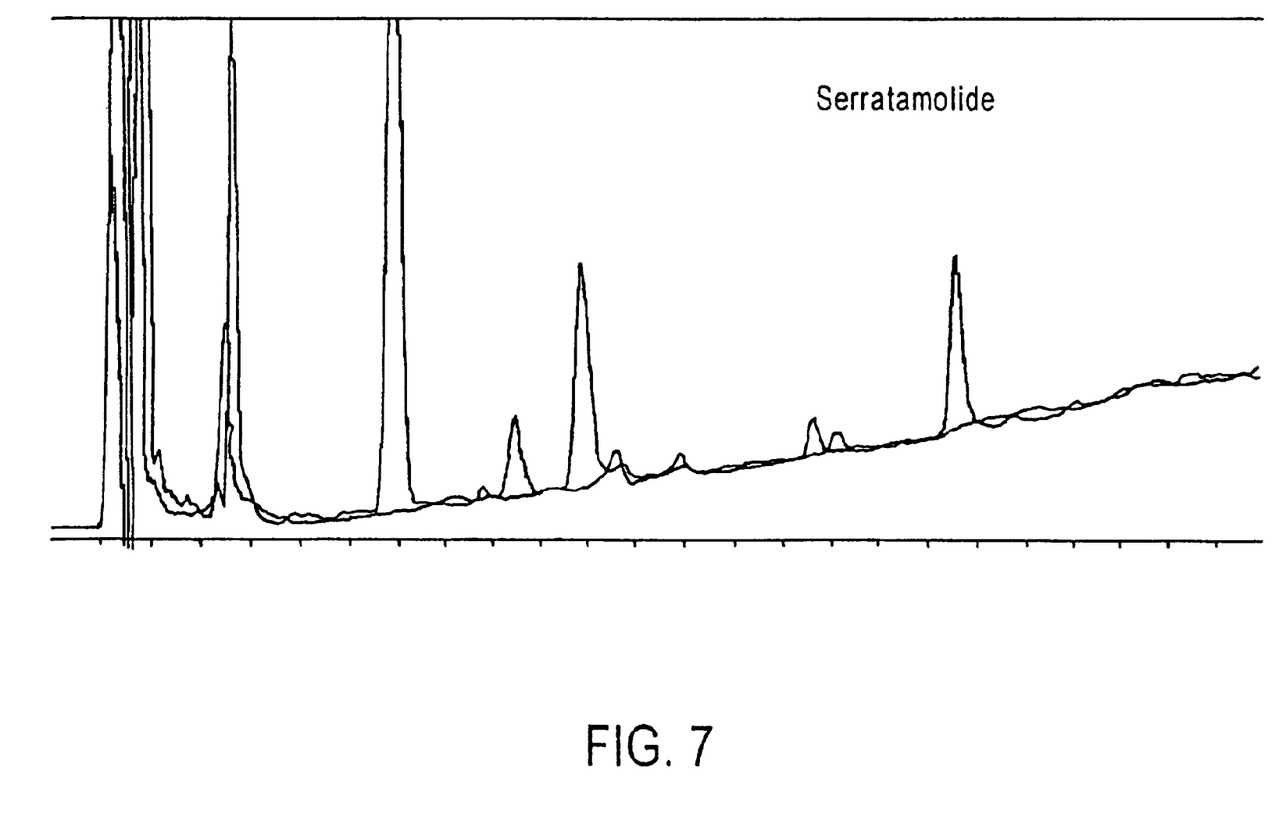
FIG. 7 shows the hydrolysis in dilute base which hydrolyzes serratamolide to serratamic acid (serratamolide peak is absent in red overlay). Hydrolysis of the serratamolide peak in dilute base eliminated antioomycetous activity against *P. ultimum* (black line=before hydrolysis, red line=after hydrolysis).

Isolation and Purification of Serratamolide; Method 1. Serratamolide is a cyclic peptide (Wasserman, H. H., et al. (1962) *J. Am. Chem. Soc.* 84, 2978–2982). In this EXAMPLE, Serratamolide was isolated from liquid cultures of *Serratia marcescens* and purified from a 50% to 75% methanol solid phase extraction (SPE), then separated by preparative HPLC (FIG. 3).

Bacterial cultures were grown in peptone-glycerol-phosphate (PGP) medium, or in a soytone medium as described by Strobel, G. et al. (1999) *Microbiol.* 145: 3557–3564. PGP consisted of 5 g bacto-peptone, 10 ml glycerol, and 2 g dibasic potassium phosphate (per liter). For maintenance, bacterial cultures grown on potato dextrose agar (PDA) for 2 to 3 days were used to inoculate 20 ml of PGP broth in 250-ml flasks. After 24 hours of growth, 0.8 ml of culture broth and 0.2 ml glycerol were placed into microfuge tubes and stored at 80° C. For isolation of antioomycetous compounds, 500 ml flasks containing 100 ml of media were inoculated with 100 µl of glycerinated stock *S. marcescens* cultures. Flasks were incubated at 27° C. rotating at 90 rpm. To monitor culture growth, at 12 to 24 hour intervals, 0.5 ml of the culture broth was removed, diluted to 3 ml using sterile nanopure water, and the culture density measured at a wavelength of 660 nm.

Cultures were acidified to pH<3 using 6N HCl and diluted to 50% methanol using reagent grade methanol. Samples were centrifuged at 7,500 rpm for 25 minutes, and the supernatant passed through a 1000 mg Bond Elute C-18 solid-phase extraction cartridge (Varian) that had been equilibrated with 50% methanol. The cartridge was washed with 50% methanol, and serratamolide eluted with 12 ml of 75% methanol. This separation retained prodigiosin on the solid phase extraction cartridge. The 75% fraction was lyophilized and re-dissolved into a minimal volume of 100% methanol.

This 75% methanol fraction contained four compounds known to exhibit activity against *P. ultimum*. Serratamolide was isolated by high performance lipid chromatography (HPLC) and bioassayed against *Pythium ultimum*.

Zone of Clearing. The zone of clearing on a PDA plate measured antioomycetous activity. Oomycete cultures were grown for three to five days on PDA plates at 23° C. to produce active colonies. Compounds to be tested were placed on a PDA plate in 10 to 20 µl of methanol and allowed to dry. Then 7-mm agar plugs were cut from agar plates containing the fungal strain to be tested and seeded 10 to 15 mm away from the applied test material. Antioomycetous activity was evidenced as a zone of inhibition of growth around the test compound.

Prodigiosin Isolation. After collecting the 75% methanol fraction containing serratamolide from the solid phase cartridge, prodigiosin was eluted using $CHCl_3$:methanol (1:2), and the spectra determined on a UVICON 860 scanning UV spectrophotometer. Pigment concentration was determined by the absorbance at 540 nm.

Figure 8:
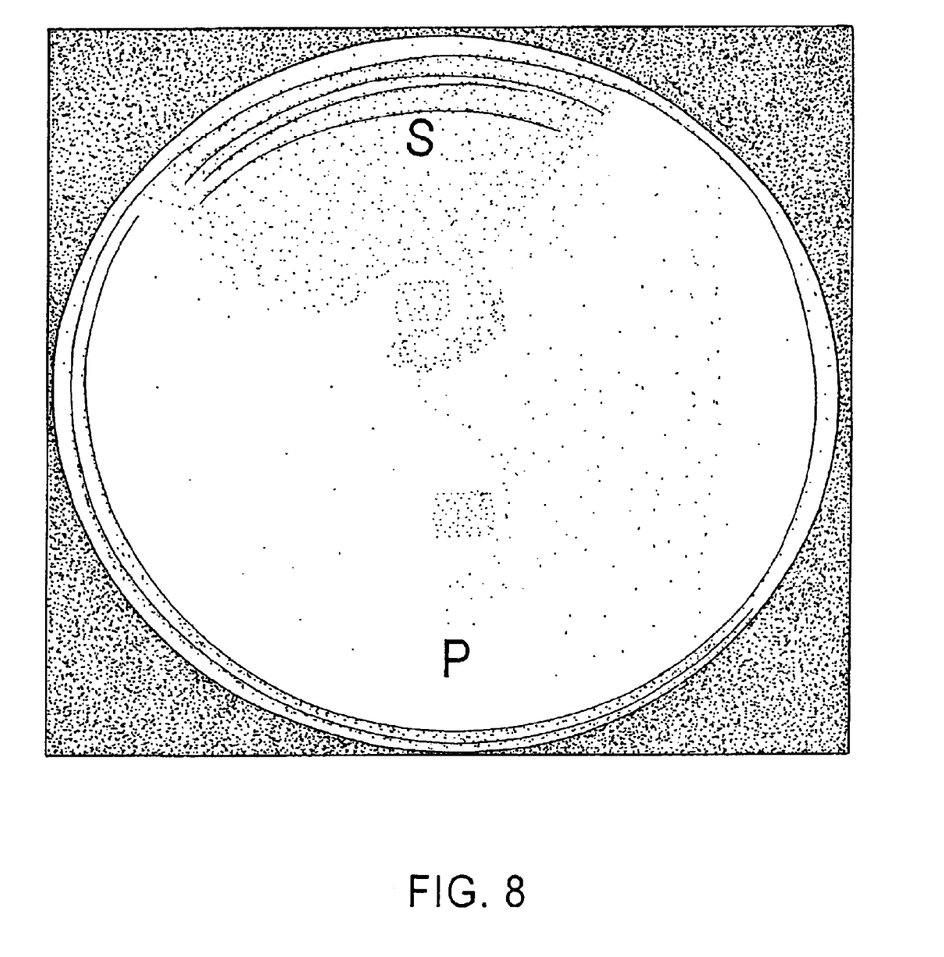
FIG. 8 shows the growth of *S. marcescens* MSU-97 and prodigiosin and serratamolide production in PGP medium. *S. marcescens* MSU-97 grown in PGP medium initiated serratamolide production approximately 12 hours after inoculation of the culture. In PGP medium, the red pigment prodigiosin was produced during exponential growth and declined as cultures entered stationary phase. The activity of a supernatant fraction against *P. ultimum* was compared with activity of a membrane fraction. All of the serratamolide was contained in the supernatant (FIG. 3). Note clearing of the plate in the region where 20 µl of the supernatant was applied (s=supernatant, p=pellet).

In this EXAMPLE, prodigiosin synthesis reached a maximum at 48 hours and then declined. Serratamolide was not produced prior to pigment synthesis, but continued after pigment synthesis decreased (FIG. 8).

To determine that MSU-97 and serratamolide were excreted into the external medium rather than being bound into the cell wall, liquid cultures were grown in PGP medium for 4 to 5 days (for time course assays, 3 ml of culture broth were removed every 12 to 24 hours). 4 ml of culture broth was removed from a 5-day liquid culture of *Serratia marcescens*. The sample was centrifuged for 15 minutes at 15,000 rpm. The supernatant was collected, lyophilized and labeled "supernatant". The pellet was resuspended in a 1:50 dilution of Tris-acetate EDTA (TAE) buffer (pH 7.5) and centrifuged for 15 minutes. The supernatant was discarded and the pellet once again resuspended in TAE. The resuspended pellet was placed in a 100-ml beaker on ice and the cells sonicated. DNAase (1 µg/ml) was added, and after 20 minutes the sample was centrifuged at 60,000×g for 1 hour to pellet a fraction containing cell wall and membrane. The pellet was extracted into acetone, lyophilized and labeled "pellet". Both samples were redissolved into 200 µl methanol, tested for activity against *P. ultimum* and analyzed for the presence of serratamolide by HPLC.

Figure 9:
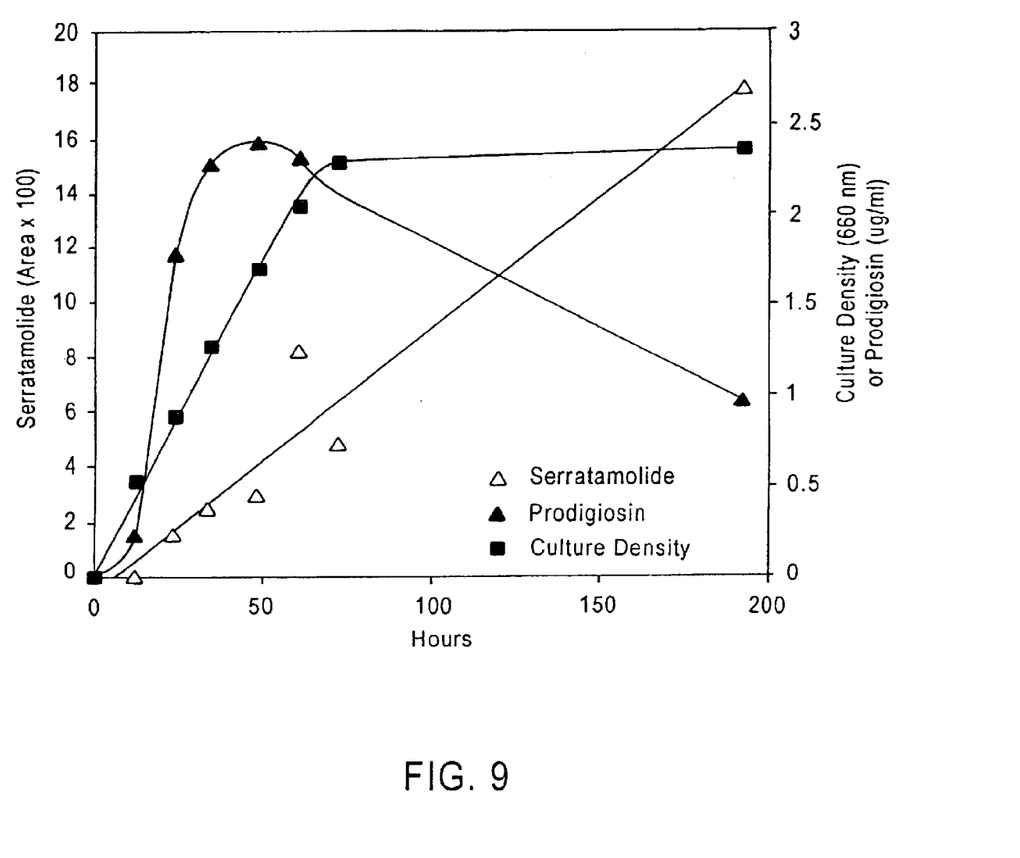
FIG. 9 is a graph showing that *S. marcescens* MSU-97 grown in PGP medium released serratamolide into the external medium rather than binding it into a membrane fraction (s=supernatant, p=acetone extracted membrane fraction).

Although previous studies found serratamolide to be associated with the bacterial membrane (Miyazaki, Y., et al. (1993). *FEMS Immunol. Med. Microbiol.* 6, 265–272.), this experiment showed that serratamolide was being released into the extracellular medium by the strain MSU-97 (FIG. 9).

HPLC Analysis. Analytical HPLC analysis was performed using a step gradient separation on a Phenomenex Phenosphere C-18 column (4.6 mm×150 mm). Solution A was 10% HPLC-grade acetonitrile:0.1% TFA in nanopure water. Solution B was 90% acetonitrile:0.1% TFA in nanopure water. The flow rate was 1 ml/min and peak detection was done at 210 nm using a variable wavelength LDC Analytical Spectromonitor 3100 detector. The solvent delivery system was a Thermo Separation Consta Metric 4100 quaternary pump. An identical gradient was used for preparative isolation of serratamolide; however, a Whatman Partisil ODS-3 column (10 mm×250 mm) was employed at a flow rate of 3 ml/min. Compounds of interest were collected in small glass vials, lyophilized, and re-dissolved into a minimal volume of methanol. The gradients utilized in the separation of serratamolide by analytical and preparative HPLC are shown in TABLE 1.

TABLE 1

| Gradient used to separate serratamolide by HPLC | | | | | |
|---|---|---|---|---|---|
| Time (min) | 0 | 2 | 20 | 30 | 35 |
| % A | 60 | 60 | 25 | 22 | 60 |
| % B | 40 | 40 | 75 | 78 | 40 |

Antioomycetous Activity of Serratamolide. Serratamolide is a previously discovered cyclic depsipeptide known to have slight antibiotic properties, to inhibit phagocytosis by polymorphonuclear leukocytes, and to increase potassium movement out of bacterial membranes. The data in this EXAMPLE shows that serratamolide is present in sufficient concentration during growth of *S. marcescens* MSU-97 to contribute significantly to the antifungal activity exhibited by this organism.

However, tests designed to determine minimum inhibitory concentrations against a number of plant fungal pathogens showed that serratamolide was active primarily against Oomycetes at concentrations between 6 and 60 µg/ml (TABLE 2). 900 µl of potato dextrose broth was placed into the wells of a sterile 24-well culture plate. Serratamolide (in methanol) was added to the wells in concentrations of 0, 3.3, 10, 33 and 100 µg/ml. 20 µl methanol was added to one row to serve as a control. Fungal cultures to be tested were grown on PDA plates for three to five days. Pieces of agar containing the cultures were transferred to sterile microfuge tubes containing 0.5 ml sterile distilled water and broken up using a sterile Teflon pestle. 100 µl of PD broth containing the mycelia was added to each well, and growth inhibition was monitored over 3 days. At the end of 3 days cultures were transferred to a ground glass homogenizer, gently broken up, diluted in distilled water and the optical density measured using a Spectronic 20 spectrophotometer at 660 nm. The minimum inhibitory concentration was determined as the concentration of serratamolide compound needed to effect a 10% reduction in growth.

Serratamolide was active against Oomycetes only (e.g., *P. cactorum, P. capsici, P. ultimum*).

TABLE 2

| Pathogen | Minimum inhibitory concentration (μg/ml) |
|---|---|
| *Phytophthora cactorum* | 60 |
| *Phytophtora parasitica* | 6 |
| *Phytophthora capsici* | 10 |
| *Pythium ultimum* | 6 |
| *Rhizoctonia solani* | >100 |
| *Botrytis cinera* | >100 |

EXAMPLE 3

Suppression of *Phyphtora parasitica* Infection of Vinca (*Catharanthus Roseus*) by an Extract of Medium Used to Culture *Serratia marcescens* MSU-97

This EXAMPLE shows the ability of extracts of *Serratia marcescens* MSU-97 to effectively limit or prevent infection of the ornamental plant Vinca (*Catharanthus roseus*) by the pathogen *Phytophtora parasitica*.

*Phytophtora parasitica* is a virulent pathogen of Vinca, except in those varieties where resistance has developed. Infection of lateral stem tissue is common and is followed by rapid damage to and death of stem tissue below the site of infection. Sometimes the plant will respond by limiting the infection at a node and abscissing leaf and stem tissue. In more severe cases, the entire plant may die. Infection by *P. parasitica* is readily induced by growing active cultures of the pathogen in a sterile capsule and inverting the capsule over a cut stem or petiole for a period of 24 hours. This infection method provides a ready test system for evaluating the efficacy of a particular compound to either prevent or cure infection by this pathogen.

Materials and Methods. Seedlings of Vinca (*Catharanthus roseus* sp.) were obtained at a local nursery and propagated vegetatively. Plants were maintained under greenhouse conditions with day temperatures of 78° F. and 64° F. to 68° F. nights. A 16-hour light, 8 hour dark cycle was maintained through the use of auxiliary overhead lighting consisting of a mixture of 400 watt metal halide and 400 watt high pressure sodium lamps. Water was supplied every other day and fertility was supplied as weekly applications of a 20-20-20 fertilizer plus micronutrients. No pesticide applications were necessary during the course of the trials.

Compound of the Invention. *Serratia marcescens* MSU-97 was grown for a period of 12 days according to the method of Strobel, G. et al. (1999) *Microbiology* 145: 3557-3564. Cultures were transferred to 250 ml centrifuge bottles and centrifuged in a Sorval Instruments GSA rotor at 20,000× g for 15 minutes to remove the cells. The supernatant was then decanted and lyophilized almost to dryness. The culture medium was acidified to a pH of 3.0 using 2N HCl and brought to 50% methanol (v/v) (Fisher Chemical). This solution was then passed through a 6 ml×1000 mg Bond Elut C-18 solid phase extraction (SPE) cartridge Varian Instruments). The column was prepared for use by washing it with 100% methanol followed by 10 ml of 18 megohm water, and 10 ml of 50% methanol. The column was then rinsed using 6 ml of 50% methanol. This retained all four of the antifungal (or antioomycetous) compounds identified in *S. marcescens* MSU-97 extracts on the column. The compounds were then eluted from the SPE cartridge using 10 ml of 100% methanol, lyophilized to dryness, and weighed.

Separation of components in the mixture was done by HPLC using a Phenomenex Phenosphere C18 column (150 mm×4.6 mm) and a step gradient from 40% acetonitrile/water +0.1% trifluoroacetic acid (TFA) to 60% acetonitrile/water +0.1% TFA (TABLE 1). Identification was made using a SpectroMonitor 3100 variable UV/VIS detector set at 210 nm. Absence of an extinction coefficient for serratamolide due to an appropriate chromophore, and the two other components, prevented quantification of individual compounds. Therefore, for purposes of this test, the qualitative presence of these compounds was noted, and the concentration of material supplied measured as the weight of extract supplied per volume of solvent (μg/ml).

Application of Compound of the Invention to Plants. Lateral shoots were cut below the terminal leaves, rinsed, dried, and left untreated (control), treated with a 10 μl drop of methanol to the end of the stem, or 10 μl of the extract dissolved in methanol. Sometimes, a small atomizer that would spray regulated volumes to the stem was employed. This material was allow to dry and then one of two tests conducted:

In test 1, 10 μl of a solution containing 6 μg/ml of extract from *S. marcescens* MSU-97 medium was applied directly to the cut stem of each of 8 plants. In parallel treatments, 10 μl of methanol, the solvent for MSU-97 extract, was applied to each of 8 plants as a positive control and allowed to dry. Leaves were excised from lateral stems of 8 additional plants and left untreated. Then capsules containing active cultures of *P. parasitica* were inverted over four plants of each of the treatments, yielding a total of six treatments with four replications, where each plant was treated as a replication.

In test 1, the pathogen was left in contact with the plant for 24 hours, the capsule removed, and the plants evaluated for damage five days after the initiation of the test. The test was repeated twice, and the data is the average of the replicated treatments for two tests.

In test 2, a similar design was employed, but the cultures of *P. parasitica* were left in contract with the stems throughout the 5-day period of the trial.

Collection and analysis of data. Damage to plants due to infection of the pathogen was ranked on a scale of 0 to 5, with 0 indicating no damage and 5 indicating substantial damage (more than 3 inches of stem visibly damaged) or death of the plant. The statistical analysis was performed using SPSS Version 10.

Results and Discussion. The data in this EXAMPLE showed that *P. parasitica* readily infected Vinca after 24 hours of exposure to the pathogen. The infection was not significantly more severe after the 96-hour exposure. Application of a 6 μg/ml of an extract to the cut surfaces of the stems prior to exposure to the pathogen reduced the incidence or severity of infection by 65% after 24-hour exposure to the pathogen and 42% after a 96-hour exposure to the pathogen. Pretreatment with methanol did not produce a significant effect on the severity of infection.

TABLE 3

Step gradient used in separation of bioactive components of *S. marcescens* MSU-97.

| Time (minutes) | % A | % B |
|---|---|---|
| 0 | 0 | 40 |
| 2 | 60 | 40 |
| 14 | 30 | 70 |
| 25 | 22 | 78 |
| 30 | 60 | 40 |

TABLE 4

Effect of an extract from culture medium of *Serratia marcescens* MSU-97 to inhibit infection of Vinca by the pathogen *Phytophtora parasitica* following 24-hour or 96-hour exposure to the pathogen. Numbers in an individual column followed by different letters are significantly different. A rating of "5" implies visible infection through more than 3 inches of leaf. A rating of "0" indicates no apparent damage.

| Treatment | Treatment No | Duration of exposure to *P. parasitica* 24 hour | 96 hour |
|---|---|---|---|
| Control | 1 | 0 a | 0 a |
| 10 µl methanol | 2 | 0 a | 0 a |
| 10 µl extract (6 µg/ml w/v) | 3 | 0 a | 0 a |
| *Phytophtora parasitica* (1 + 4) | 4 | 5 b | 4.75 b |
| Treatment 2 + 4 | 5 | 4.5 b | 4.25 b |
| Treatment 3 + 4 | 6 | 1.75 c | 2.75 c |

The foregoing description has been presented only for the purposes of illustration and is not intended to limit the invention to the precise form disclosed, but by the claims appended hereto.

We claim:

1. A method of controlling or preventing Oomycete pathogen infestation of a plant, comprising treating said plant with an effective amount of a composition containing serratamolide obtained from *Serratia marcescens*.

2. The method of claim 1, wherein the Oomycete pathogen is selected from the group consisting of *Leptomitus, Brevilegnia, Aphanoinyces, Achlya, Saprolegnia, Pythium, Plasmopara, Phytophthora, Peronospora* and *Albugo*.

3. The method of claim 1, wherein the method of treating is selected from the group consisting of foliar application, application to the aerial portion of the plant, application to the soil around roots of the plant wherein the compound is in a liquid form, application to the soil around roots of the plant wherein the compound is in a granular form, and incorporation in a plant cell culture medium.

4. The method of claim 1, wherein the concentration of serratamolide in the composition is between 6 and 100 µg/ml.

5. The method of claim 1, wherein the *Serratia marcescens* is *Serratia marcescens* MSU-97.

6. The method of claim 1, wherein the composition comprises serratamolide and oocydin A.

7. The method of claim 1, wherein the composition further comprises carrier carriers and/or additives.

8. The method of claim 7, wherein the composition further comprises a fertilizer.

9. The method of claim 1, wherein the plant is selected from the group consisting of cereals, beets, stone fruit plants, soft fruit plants, leguninlous plants, oil plants, cucumber plants, fiber plants, citrus fruit plants, vegetables, lauraceae, tobacco, nut plants, coffee, sugar cane, tea, vines, hops, banana plants, natural rubber plants, and ornamental plants.

10. The method of claim 1, wherein the composition comprises a mixture of *Serratia marcescens* MSU-97, serratamolide and oocydin A.

11. The method of claim 1, wherein the composition comprises a mixture of *Serratia marcescens* MSU-97 and serratamolide.

12. The method of claim 1, wherein the composition comprises a mixture of *Serratia marcescens* MSU-97 and oocydin A.

* * * * *